US012594423B2

(12) United States Patent
Alvord

(10) Patent No.: US 12,594,423 B2
(45) Date of Patent: Apr. 7, 2026

(54) OCCIPITAL LOBE STIMULATION DEVICE

(71) Applicant: Robert Alvord, Tualatin, OR (US)

(72) Inventor: Robert Alvord, Tualatin, OR (US)

( * ) Notice: Subject to any disclaimer, the term of this patent is extended or adjusted under 35 U.S.C. 154(b) by 45 days.

(21) Appl. No.: 18/445,891

(22) Filed: Mar. 8, 2024

(65) Prior Publication Data

US 2025/0332418 A1 Oct. 30, 2025

(51) Int. Cl.
*A61N 1/05* (2006.01)
*A61N 1/36* (2006.01)
*A61N 5/06* (2006.01)

(52) U.S. Cl.
CPC ......... *A61N 1/3606* (2013.01); *A61N 1/0529* (2013.01); *A61N 5/0622* (2013.01)

(58) Field of Classification Search
None
See application file for complete search history.

(56) References Cited

U.S. PATENT DOCUMENTS

| | | | | |
|---|---|---|---|---|
| 8,280,515 B2 * | 10/2012 | Greenspan | ........... | A61N 1/0534 607/46 |
| 8,956,396 B1 * | 2/2015 | Friend | .................. | A61N 5/0622 607/88 |
| 2022/0008746 A1 * | 1/2022 | Malchano | ............ | A61B 5/4088 |
| 2025/0332418 A1 * | 10/2025 | Alvord | ................ | A61N 5/0622 |

FOREIGN PATENT DOCUMENTS

CA 2338805 A1 * 2/2000 ........... A61N 1/0556

OTHER PUBLICATIONS

Rocca et al. Robot-assisted implantation of a microelectrode array in the occipital love as a visual prosthesis: technical note (Year: 2023).*

* cited by examiner

*Primary Examiner* — Shirley X Jian
(74) *Attorney, Agent, or Firm* — Howard Russell, Attorney at Law

(57) ABSTRACT

Occipital lobe stimulation device comprising normal looking glasses having a frame portion with side portions and lens portions, provided together with a battery-powered plurality of Light-Emitting Diodes (LEDs) fixed around an anterior periphery of the frame portion for emitting photons of light to reflect off of an object in the outside world, and a plurality of photoreceptors dispersed across and retained in the lens portions, the photoreceptors being connected via wires to corresponding inverters in the side portions which are also wire connected to output devices on a strap an enabling connection to corresponding input devices surgically implanted and connected to the user's occipital lobes, for transmitting image information relating to the object to the user's occipital lobes to enable the user's brain to make use of the information.

13 Claims, 7 Drawing Sheets

OCCIPITAL LOBE STIMULATION DEVICE

RELATED APPLICATION

This is an originally-filed US Non-provisional patent application.

FIELD OF INVENTION

This invention relates to an electromechanical Occipital Lobe Stimulation Device which takes place of the rods and cones in human eyes and transmits photostimuli to a user's occipital lobe.

BACKGROUND OF THE INVENTION

Brief Overview of the Neurophysiology of Human Sight

Referring to FIG. 1 (Prior Art), depicting a brief overview of human sight, the image 800 in front of the eye 1100, as it passes into the eye through the lens 1112, is inverted (as shown at 801) and is set upon the rods and cones 1113 in the back of the eyeball 1111. This inversion is useful as it allows the eye to judge the distance of the object.

This inverted image 801 is sent to the occipital lobe 1100 (of a human brain 1000) via the optic nerve 1110.

The brain 1000 of a person, including the occipital lobe 1100, interprets this inverted input, namely the image 801, by constructing a perception for the person that aligns with the persons view of the image from their current physical orientation, i.e., so that the image appears upright to the person. In this way, the brain 1000 can make a more coherent use of the information for the person's benefit.

SUMMARY

An Occipital Lobe Stimulation Device is designed to take the place of a user's, or patient's eye and to send information from the outside world to the patient's occipital lobe.

Glasses With Light Emitting Diodes (LEDs) and Photoreceptors

There are provided glasses comprising a plurality of lenses, the glasses further comprising a frame portion, the frame portion further comprising a bridge portion located between lens-retaining portions of the frame, the frame portion further comprising side portions (that is, such as glasses temples portions) the glasses appearing from the outside to be a normal pair of sunglasses.

Further, there are provided Light Emitting Diodes (LEDs), which may appear as dots or circles along an anterior surface of the outside of the frame surrounding the lenses which emit light (the LEDs in a finished product will not be noticeable). There is also provided a USB rechargeable battery inside the bridge portion of the glasses frame portion to power the LEDs.

Photons of light emitted from the LEDs will "bounce off" (that is to say, "reflect off") the object in front and return to the lenses.

Inside the lenses there are provided photoreceptors, which may appear as dots or as small circles as shown in the FIGS. hereof.

The photoreceptors receive the photons of light which have bounced back from the object, and these take the place of or act similarly as would normally functioning, or normally existing, rods and cones in the eye.

Each photoreceptor is connected to a wire which carries reflected light image-related information to the side portions of the frame portion. There are an equal number of receptors in a top half of each lens as a bottom half of each lens. This is for a very specific reason as stated later.

The number of photoreceptors is variable and dependent upon each patient's health and functionality of their occipital lobe. The occipital lobe of a patient who has been blind for five years may not be able to handle as many photoreceptors as a recently blind patient.

The Inverter

There is provided an inverter that lies within the side portions of the glasses and receives the wires and information from the wires which connect to the photoreceptors in the lenses.

The image from the outside, as it enters the eye, is inverted and is set upon the rods and cones of a normally functioning eye. The inverter of the present invention accomplishes this task.

There is an equal number of receptors in the top half of the lenses as the bottom half.

The inverter will take the top of the receptors and invert them such that the topmost input wire becomes the bottommost.

Each lower wire of the top half is inverted such that the second wire from the top becomes the second wire from the bottom and so on.

The same is true for the bottom set of input wires: the bottommost wire becomes the topmost of the inverter, with the second wire from the bottom becoming the second wire from the top and so on.

The patient will have the option to not have the inverter and the wires travel straight from the photo receptors to the rear (adapted to be near the occipital lobe of the patient). While it is less expensive and the brain does have the ability to learn to invert the image on its own, this will take much longer and would produce more side effects such as headache and nausea. In this way, the photo receptor wire order mimics the order of the inversion process that takes place in a person's normally functioning eyes, rods and cones, optic nerves, and occipital lobes.

Output Devices and Input Devices

There are further provided output devices and input devices, the output devices comprising notches and the input devices comprising protrusions corresponding with the notches of the output devices. The protrusions of the input devices insert into the notches of the output devices: this ensures that the wires from the output devices match up perfectly with pins on the input devices carrying signals to the occipital lobes.

With both the output and input devices, there are equal number of wires in the top half and bottom half, allowing better orientation and structure when the information is sent to the brain, allowing for easier understanding and less stress on both the occipital lobe and the brain.

The output devices are carried on a rear strap wearable on the patient's head, and the input devices are adapted to be implanted into the occipital lobe by a surgical procedure which removes matching holes in the skull at the location of the occipital lobe, then the optic nerve is severed where it attaches to the occipital lobe. This allows direct access to the occipital lobe where the input devices can be implanted.

Both the output devices and the input devices are magnetized strongly enough to prevent accidental separation, yet the output devices and the input devices are able to be separated when the patient desires to remove the glasses such as when going to sleep.

DETAILED DESCRIPTION

Figure 1:
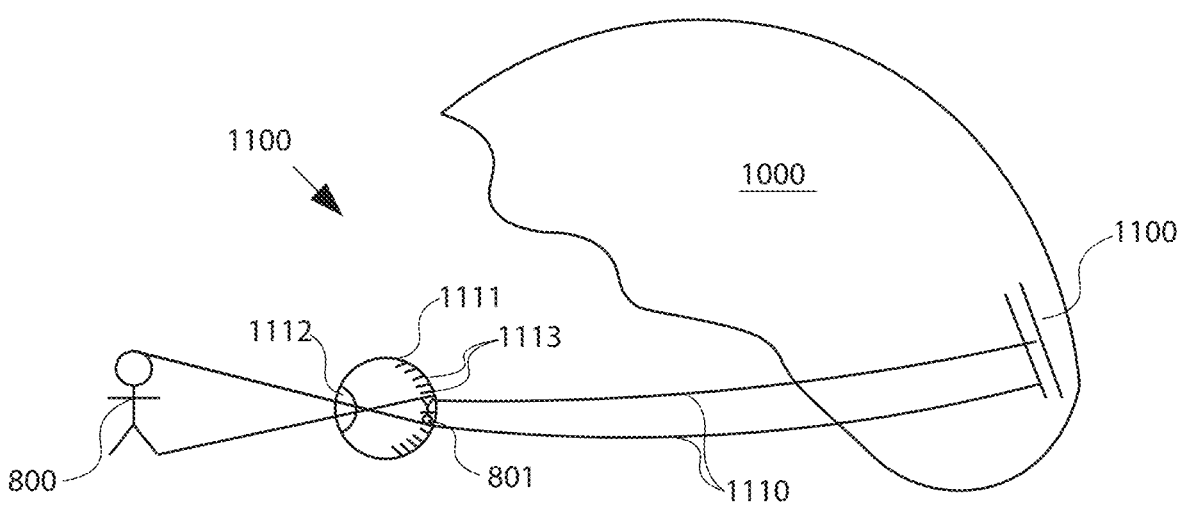
FIG. 1, labeled as Prior Art, shows a side view of a simplified illustration of a normally functioning human eye, brain, optic nerve, and occipital lobe.

Referring to the FIGS., this disclosure is of one or more devices 100 designed to be adapted to take the place of an eye 1100 to send information relating to an image 800 from the outside world to the occipital lobe portion 1100 of the user's brain 1000, the eye, the image 800, the brain 1000, and occipital lobe portion 1100 of the brain being illustrated in FIG. 1, labeled "Prior Art".

Figure 2:
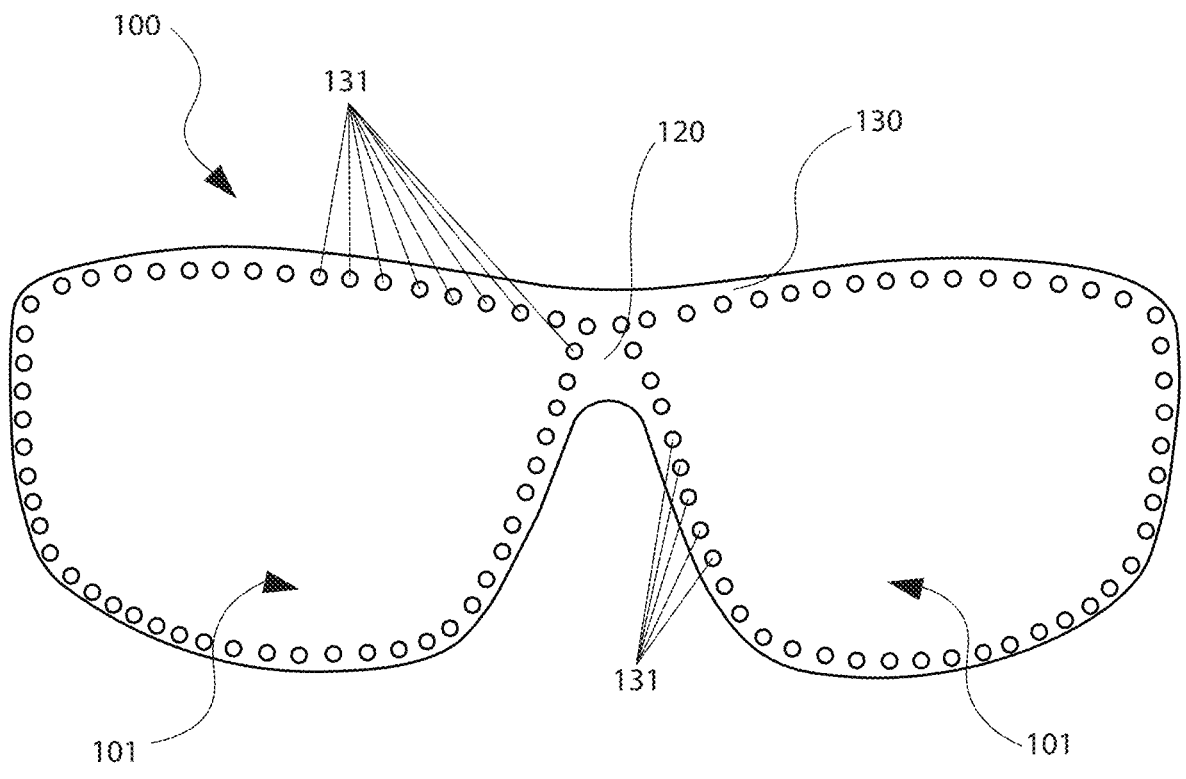
FIG. 2 shows a front perspective view of glasses with Light Emitting Diodes (LEDs) on an anterior surface of a frame portion of eyeglasses.

FIG. 2 shows a front perspective view of a glasses portion of an occipital lobe stimulation device 100 comprising a frame portion 130 defining lens retaining portions, or areas, 101, and with Light Emitting Diodes (LEDs) 131 mounted and located on an anterior peripheral surface of the frame portion 130 for lighting images presented in front of the glasses portion of the occipital lobe stimulation device 100. The frame portion further comprises a bridge portion 120, located between the lens-retaining portions 101 of the frame, and side portions (that is, glasses-type temple portions) 140.

The glasses portion of the device 100 further comprises a plurality of lenses 111, and the glasses portion of the device 100 appears from the outside to be a normal pair of sunglasses.

Further, there are provided Light Emitting Diodes (LEDs) 131, which may appear as dots along the anterior surface of the outside of the frame portion 130, surrounding the lenses 111, and which emit light. The LED's 131 in the finished product will not be noticeable when not illuminated. There is also provided a USB rechargeable battery (not shown) inside the bridge portion 120 of the glasses frame portion to power the LED's 131.

Photons of light emitted from the LEDs 131 are adapted to "bounce off" (that is to say, "reflect off") an object 800 in front of the device 100 and return image-related information to the lenses 111.

Figure 3:
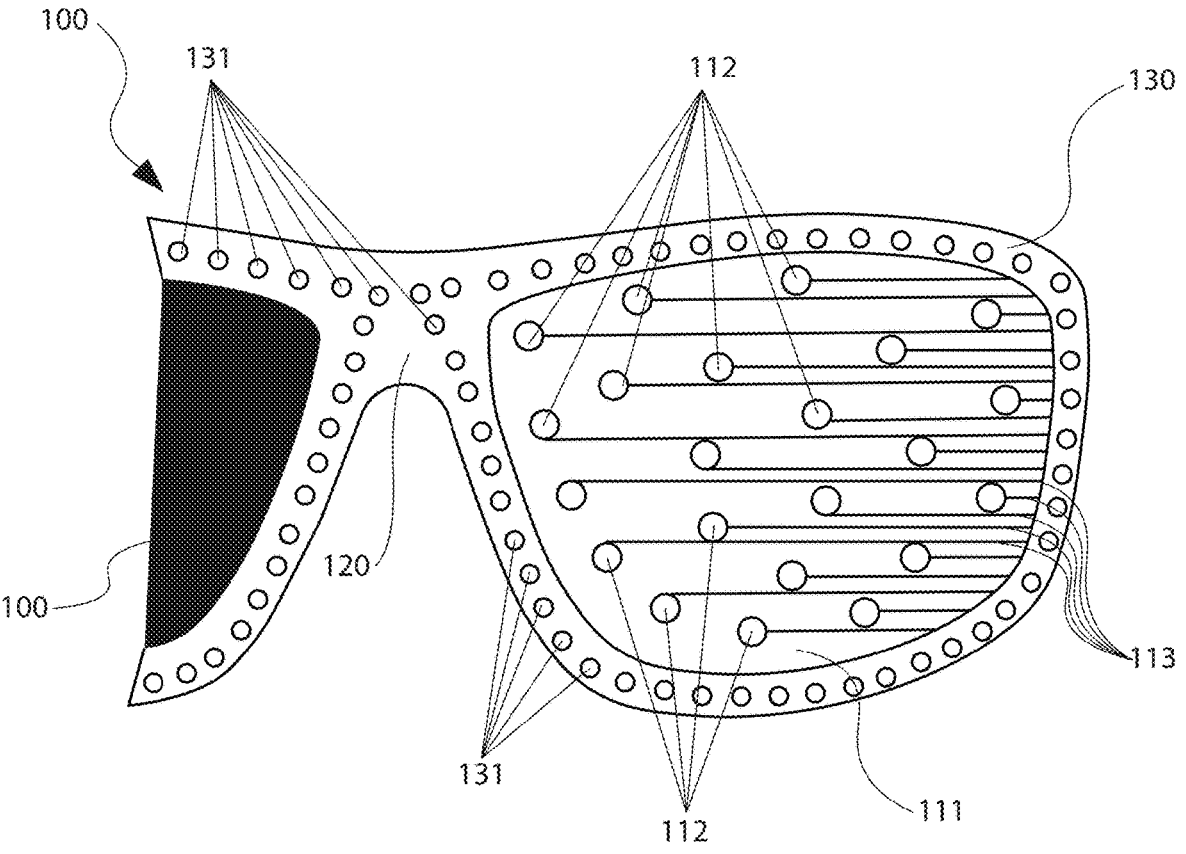
FIG. 3 shows a portion of the glasses of FIG. 2, further illustrating a plurality of photoreceptors and leads in a lens portion of the glasses.

Inside the lenses 111 there are provided photoreceptors 112 which may appear as dots or small circles as shown in FIG. 3 hereof.

The photoreceptors 112 receive the photons of light which have reflected back from the object 800, and these act as would normally-functioning, or normally-existing, rods and cones 1113 in the eye 1111 (See FIG. 1).

As shown in FIG. 3, each photoreceptor 112 is connected to a wire 113 which carries the reflected light image-related information to the side portions 140 of the frame portion 130. There are preferably an equal number of receptors 112 in a top half of each lens as in a bottom half of each lens.

The number of photoreceptors 112 may vary and is dependent upon each patient's health and functionality of their occipital lobe 1000. The occipital lobe 1000 of a patient who has been blind for five years may not be able to handle as many photoreceptors 112 as a recently blind patient.

The Inverter

Figures 4A, 4B:
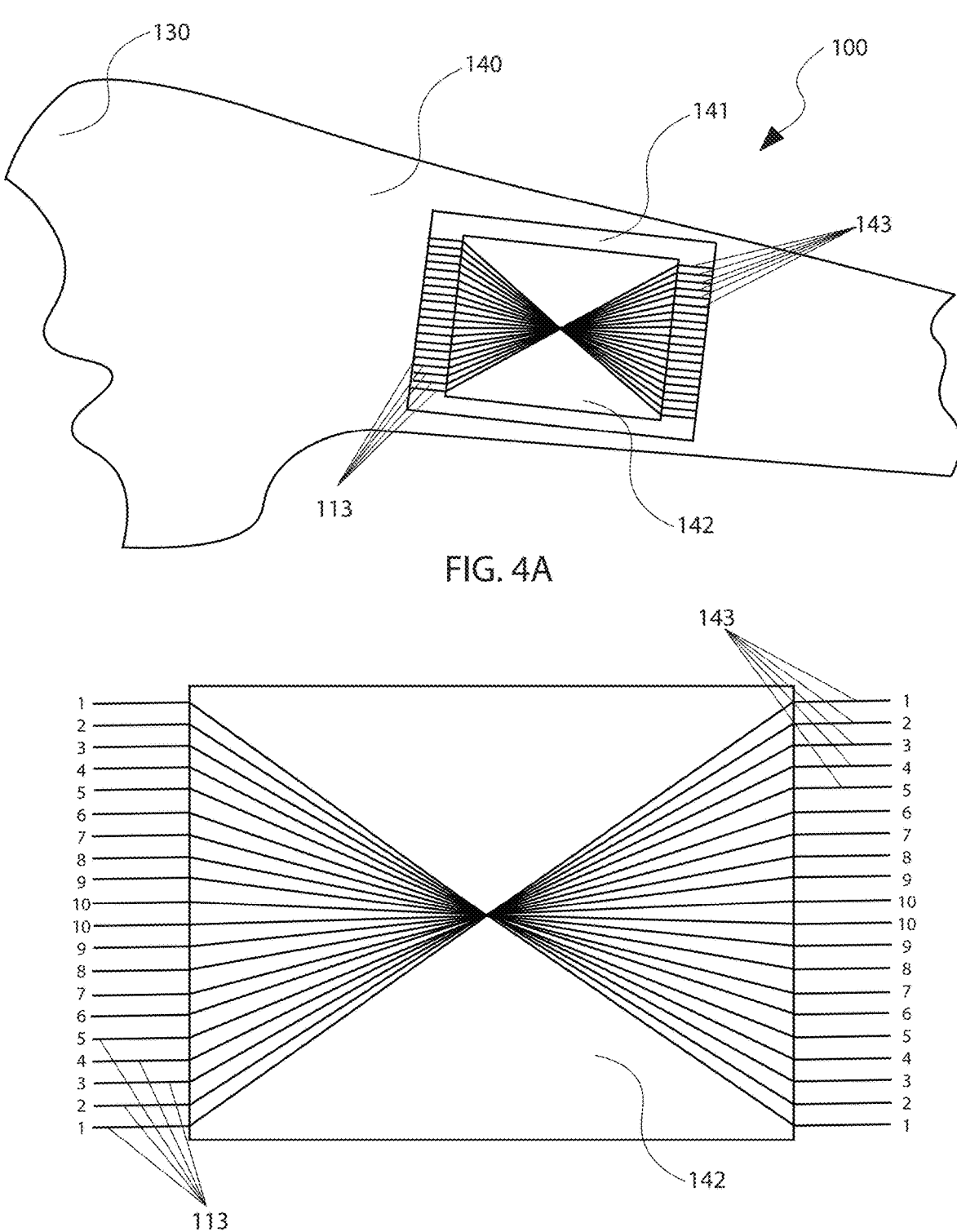
FIG. 4A illustrates a side, otherwise known as a temple, portion of the glasses frame showing retention of an inverter in a side portion of the glasses.
FIG. 4B illustrates a close-up schematic view of wiring for the inverter.
Figure 5A:
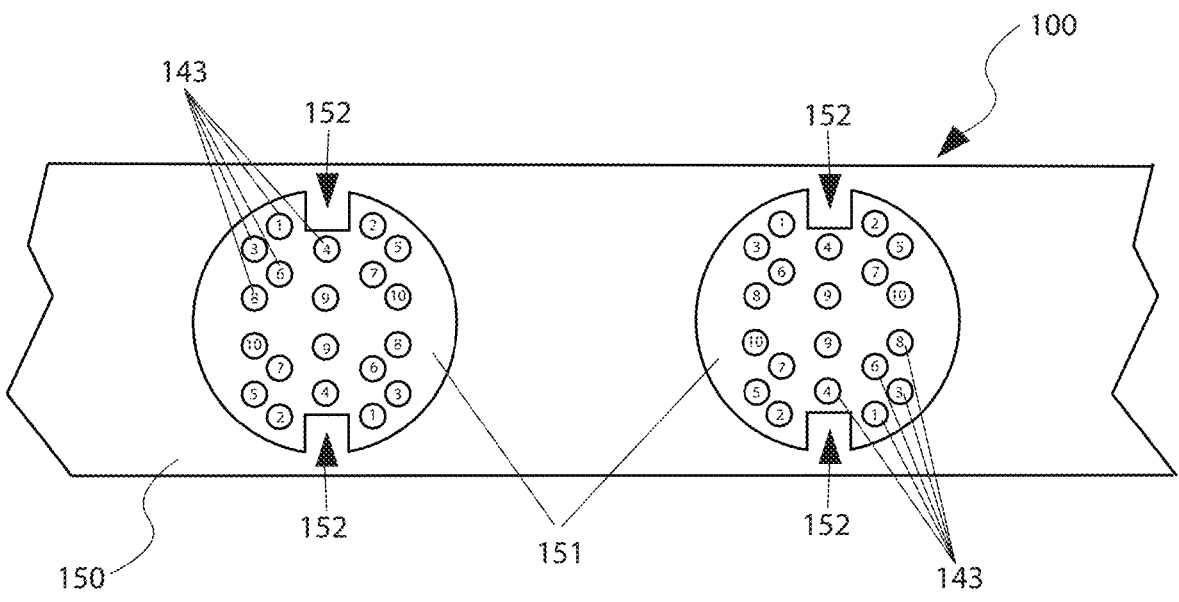
FIG. 5A illustrates a top view of a plurality of output devices on a strap together with an illustration of their pin configurations.
Figure 5B:
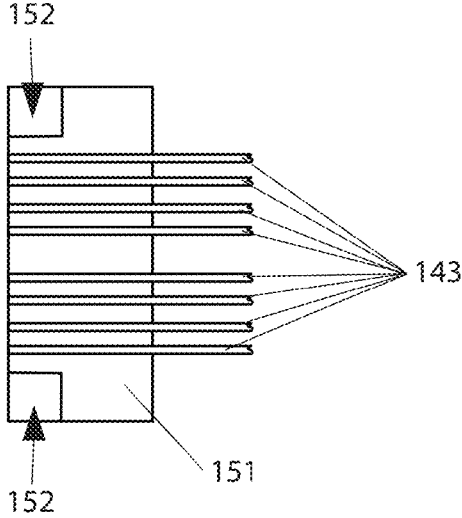
FIG. 5B illustrates a side cutaway view of an output device showing notches adapted for interconnection and orienting relative to an input device and showing the output device being adapted for orientation of the output device between wires from photoreceptors and an input device adapted for being located adjacent an occipital lobe.
Figure 6A:
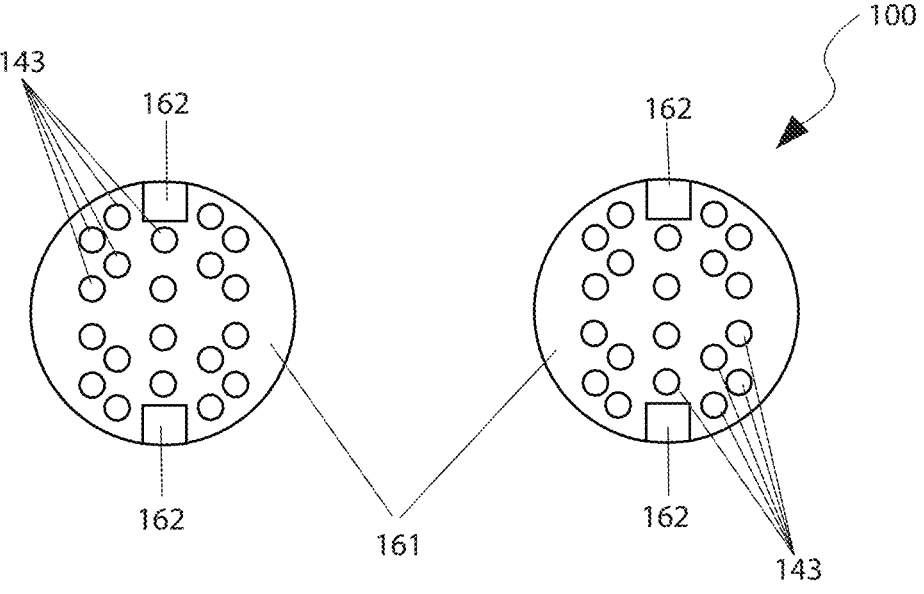
FIG. 6A illustrates a top view of a plurality of input devices adapted for surgical implantation in a user's skull adjacent occipital lobes together with an illustration of their pin configurations for the input devices corresponding with the pin configurations of the output devices of FIG. 5A.
Figure 6B:
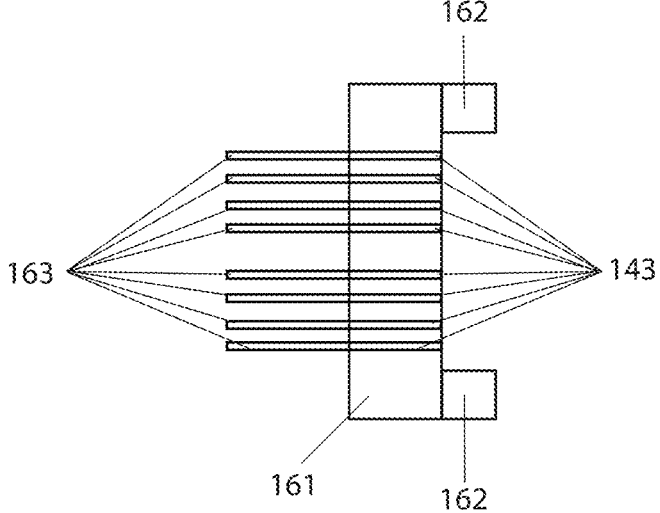
FIG. 6B illustrates a side cutaway view of an input device showing protrusions adapted for interconnection and orienting relative to an input device and showing the input device being adapted for orientation of the input device between an output device on the strap and an occipital lobe.

As shown in FIGS. 4A and 4B, there is shown an inverter 141 of the occipital lobe stimulation device 100 that lies within the side portions 140 of the glasses frame portion 130. The inverter 141 receives the wires 113, and image-related information, via the wires 113 which connect with the photoreceptors 112 in the lenses 111.

With a normally functioning eye 1100, the image 800 from the outside, is inverted as it enters the eye, is inverted as shown at 801, and is set upon the rods and cones 1113. The inverter 141 of the present invention accomplishes this task.

There is an equal number of receptors 112 in a top half of the lenses 111 as there are in a bottom half of the lenses, and the inverter 141 will receive the input from the top of the receptors 112 and invert them such that the topmost input wire becomes the bottommost output from the inverter.

Each lower wire 113 of the top half is inverted such that the second wire 113 from the top becomes the second wire 113 from the bottommost output from the inverter, and so on.

The same is true for the bottom set of input wires 113. The bottommost wire 113 becomes the topmost output of the inverter 141, with the second wire 113 from the bottom becoming the second wire 113 from the topmost output of the inverter, and so on.

The patient will have the option to not have the inverter 141 and the wires 113 travel straight from the photo receptors 112 to the rear (adapted to be near the occipital lobe 1100 of the patient). While it is less expensive and the brain 1000 does have the ability to learn to invert the image 800 on its own, this will take much longer and would produce more side effects such as headache and nausea. In this way, the photo receptor wire 113 order mimics the order of the inversion process that takes place in a person's normally functioning eyes 1111, rods and cones 1113, optic nerves 1110, and occipital lobes 1100.

Output Devices and Input Devices

As shown in FIGS. 5A-6B, there are further provided output devices 151 and input devices 161 having pin and wire configurations 143, 163 shown matching each other and the inverted wire outputs via wires 143 from each inverter 141. The output devices 151 comprise notches 152, and the input devices 161 comprise protrusions 162 corresponding with the notches of the output devices. The protrusions 162 of the input devices insert into the notches 152 of the output devices 151. This ensures that wires 143 from the output devices 151 match up perfectly with the pins on the input devices 161 for carrying signals to the occipital lobes 1100.

With both the output devices 151 and input devices 161, there are equal number of pins 143 and corresponding wires 143 in the top half and bottom half of the respective devices, matching the pin configurations 143 of each other and the wire 143 configuration output from the inverter 141 allowing better orientation and structure when the information is sent to the brain 1000, allowing for easier understanding and less stress on both the occipital lobe 1100 and the brain.

Figure 7:
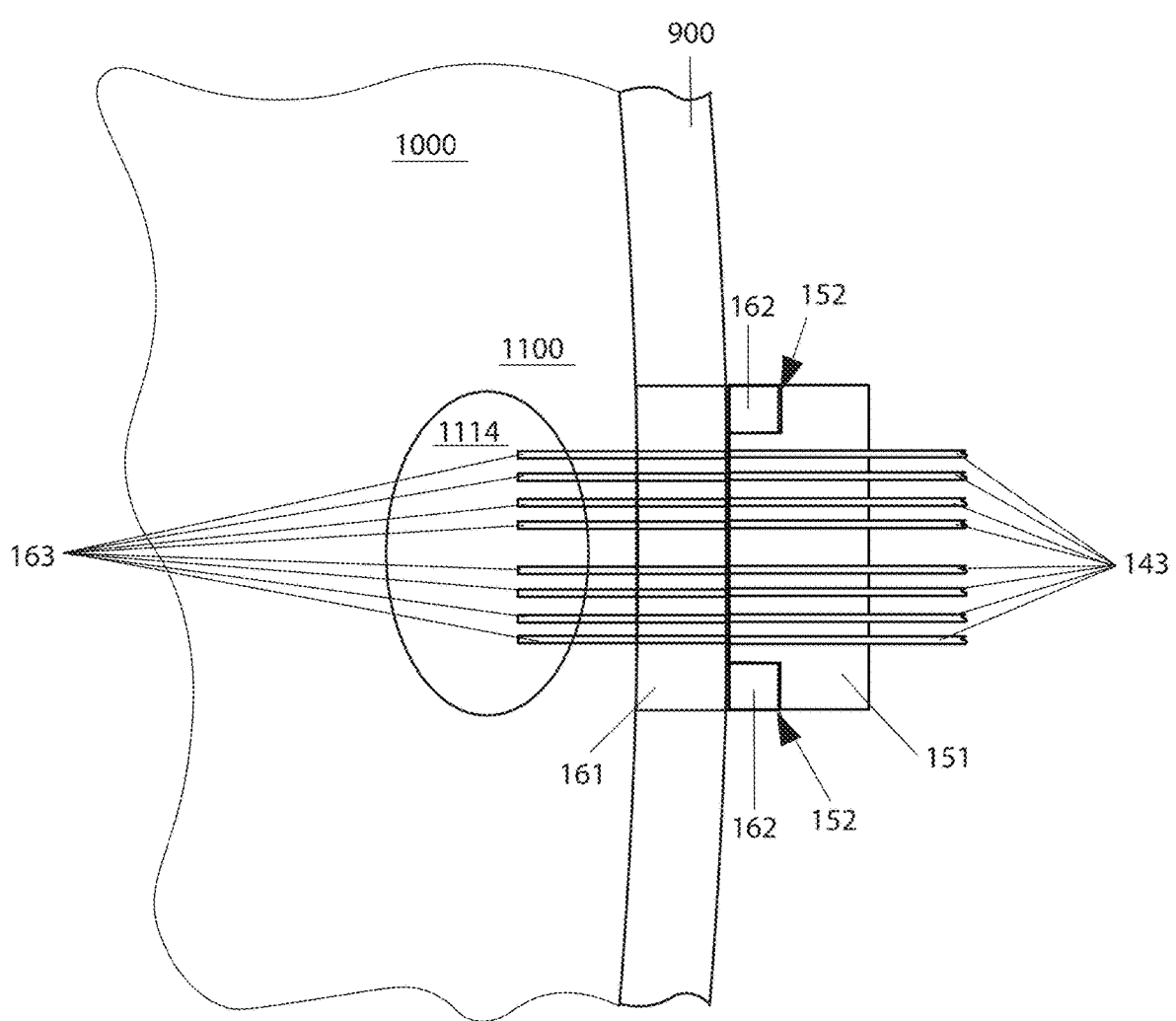
FIG. 7 illustrates a side cutaway view of an output device, with its wires leading to an inverter, adapted to be interfaced at a human skull with an implanted input device, with its wires being adapted for leading to an occipital lobe.

Referring additionally to FIG. 7, whereas the output devices 151 are carried on a rear strap 150 wearable on the patient's head, the input devices 161 are adapted to be implanted into the occipital lobe 1100 by a surgical procedure which removes matching holes in the skull 900 at the location 1114 of the occipital lobe 1100 of the brain 1000, then the optic nerve 1110 is severed where it attaches to the occipital lobe. This allows direct access to the occipital lobe 1100 where leads 163 from the input devices 161 can be implanted.

Both the output devices 151 and the input devices 163 are magnetized strongly enough to prevent accidental separation, yet the output devices and the input devices are able to be separated when the patient desires to remove the glasses portion of the occipital lobe stimulation device 100 such as when going to sleep.

I claim:

1. An occipital lobe stimulation device to enable transmission of image information pertaining to an object in the outside world to a user's occipital lobe to enable the user's brain to make use of the information, comprising:

a glasses frame portion having an anterior surface and periphery;

at least one side portion connected to said glasses frame portion;

at least one lens portion retained within said glasses frame portion;

a plurality of Light-Emitting Diodes (LEDs) fixed around the anterior surface and the periphery of said glasses frame portion, for emitting photons of light to reflect off of the object;

a plurality of photoreceptors dispersed across and retained in said at least one lens portion adapted for collecting reflected light off of the object from said plurality of LEDs;

an output device adapted for being mounted externally of the skull of the user, said output device having a plurality of inputs and a corresponding plurality of outputs, each input corresponding with and being electrically connected to one of said plurality of photoreceptors; and an input device adapted for being surgically implanted under the user's skull for connection to the user's occipital lobe, said input device having a plurality of inputs and a corresponding plurality of outputs, each input corresponding with an output of the plurality of outputs of said output device, each output of the plurality of outputs of said input device being adapted for being electrically connected with the user's occipital lobe and adapted for transmitting to the user's occipital lobe image information pertaining to the object to enable the user's brain to make use of the information.

2. The occipital lobe stimulation device of claim 1, further comprising an inverter retained in said at least one side portion and having a plurality of inputs each input corresponding to one of said plurality of photoreceptors, wherein each photoreceptor of said plurality of photoreceptors is electrically connected to a corresponding input of said inverter, said inverter having a plurality of outputs, each output corresponding with an input of said inverter, each of the inputs of said inverter being electrically connected to its corresponding output of said inverter, and wherein each output of the plurality of outputs of said inverter is electrically connected with one of the corresponding inputs of said output device.

3. The occipital lobe stimulation device of claim 2, wherein the inputs of said inverter are inversely connected to the outputs of said inverter adapted to invert the position of each photoreceptor electrical signal as it is transmitted to the occipital lobe.

4. The occipital lobe stimulation device of claim 3, wherein each said lens portion comprises a top half and a bottom half, wherein each said output device and each said input device comprises a top half and a bottom half, wherein there are provided an equal number of photoreceptors retained in the top half of each lens portion as are retained in the bottom half of each lens portion such that there are likewise an equal number of wires in the top half of each input device and output device as there are in each bottom half of each input device and output device.

5. The occipital lobe stimulation device of claim 4, wherein said output device and said input device each comprise a plurality of interconnection portions for holding said output device and said input device in fixed proximity interconnected to each other, thereby assuring the electrical interconnection of the output of the output device with the input of the input device.

6. The occipital lobe stimulation device of claim 5, wherein said interconnection portion of said output device comprises a plurality of protrusions, and wherein said interconnection portion of said input device comprises a plurality of notches corresponding in number and location with the plurality of protrusions of said output device.

7. The occipital lobe stimulation device of claim 6, wherein said plurality of protrusions and said plurality of notches are magnetized to prevent accidental separation but to otherwise allow desired separation.

8. An occipital lobe stimulation device to enable transmission of image information pertaining to an object in the outside world to a user's occipital lobe to enable the user's brain to make use of the information, comprising:

a glasses frame portion having an anterior surface and a periphery;

at least one side portion connected to said glasses frame portion;

a plurality of lens portions retained within said glasses frame portion;

a plurality of Light-Emitting Diodes (LEDs) fixed around the anterior surface and the periphery of said glasses frame portion, for emitting photons of light to reflect off of the object;

a plurality of photoreceptors dispersed across and retained in said plurality of lens portions adapted for collecting reflected light off of the object from said plurality of LEDs;

an inverter retained in said at least one side portion, said inverter comprising a plurality of inputs, each input corresponding to one of said plurality of photoreceptors, wherein each photoreceptor of said plurality of photoreceptors is electrically connected to a corresponding input of said inverter, said inverter having a plurality of outputs, each output corresponding with an input of said inverter, each of the inputs of said inverter being electrically connected to its corresponding output of said inverter;

an output device adapted for being mounted externally of the skull of the user, said output device having a plurality of inputs and a corresponding plurality of outputs, each input corresponding with and being electrically connected to one of said plurality of outputs of said inverter; and an input device adapted for being surgically implanted under the user's skull for connection to the user's occipital lobe, said input device having a plurality of inputs and a corresponding plurality of outputs, each input corresponding with an output of the plurality of outputs of said output device, each output of the plurality of outputs of said input device being adapted for being electrically connected with the user's occipital lobe and adapted for transmitting to the user's occipital lobe image information pertaining to the object to enable the user's brain to make use of the information.

9. The occipital lobe stimulation device of claim 8, wherein the inputs of said inverter are inversely connected to the outputs of said inverter adapted to invert the position of each photoreceptor electrical signal as it is transmitted to the user's occipital lobe.

10. The occipital lobe stimulation device of claim 9, wherein each said lens portion comprises a top half and a bottom half, wherein said output device and said input device each comprise a top half and a bottom half, wherein there are provided an equal number of said plurality of photoreceptors retained in the top half of each said lens portion as are retained in the bottom half of each said lens portion such that there are likewise an equal number of inputs in the top half of said input device and said output device as there are in each bottom half of said input device and said output device.

11. The occipital lobe stimulation device of claim 10, wherein said output device and said input device each comprise a plurality of interconnection portions for holding said output device and said input device in fixed proximity interconnected to each other, thereby assuring the electrical interconnection of said output device with said input device.

12. The occipital lobe stimulation device of claim 11, wherein said interconnection portion of said output device comprises a plurality of protrusions, and wherein said interconnection portion of said input device comprises a plurality of notches corresponding in number and location with the plurality of protrusions of said output device.

13. The occipital lobe stimulation device of claim 12, wherein said plurality of protrusions and said plurality of notches are magnetized to prevent accidental separation but to otherwise allow desired separation.

* * * * *